United States Patent [19]

Chiang et al.

[11] Patent Number: 4,485,174

[45] Date of Patent: Nov. 27, 1984

[54] HEMOGLOBIN-BASED BLOOD GAS CONTROL

[75] Inventors: Ching Chiang, Acton; Susan K. Bolton, Wayland, both of Mass.

[73] Assignee: Instrumentation Laboratory Inc., Lexington, Mass.

[21] Appl. No.: 427,470

[22] Filed: Sep. 29, 1982

[51] Int. Cl.³ .................... C12Q 1/32; G01N 33/96; G01N 33/72

[52] U.S. Cl. .................... 436/11; 424/101; 435/2; 435/25; 435/26; 436/15; 436/18

[58] Field of Search .................... 436/10, 11, 18, 15; 424/101; 435/2, 25, 26

[56] References Cited

U.S. PATENT DOCUMENTS

| | | | |
|---|---|---|---|
| 3,466,249 | 9/1969 | Anderson | 436/11 |
| 3,859,049 | 1/1975 | Ware et al. | 436/11 |
| 3,973,913 | 8/1976 | Louderback | 436/10 |
| 4,001,142 | 1/1977 | Turner | 436/11 |
| 4,049,673 | 9/1977 | Scheinberg | 424/101 |
| 4,102,810 | 7/1978 | Armstrong | 436/18 |
| 4,112,070 | 9/1978 | Harmening | 424/101 |
| 4,126,575 | 11/1978 | Louderback | 436/10 |
| 4,163,734 | 8/1979 | Soremsem et al. | 436/11 |
| 4,199,471 | 4/1980 | Louderback et al. | 436/11 |
| 4,401,122 | 8/1983 | Clark, Jr. | 128/635 |

OTHER PUBLICATIONS

C.A. 95, 121024 F, (1981).
Kuma, F., et al., J. Biol. Chem., vol. 247, No. 2, pp. 550–555, (1972).
Huennekers, F. M., et al., "Methemoglobin Reductases in Hereditory Disorders of Erythrocyte Metabolism", pp. 87–101, (1968).
Sugita, Y., et al., J. Biol. Chem., vol. 246, No. 19, pp. 6072–6078, (1971).
Yubisui, T., et al., Biochem. Biophys. Res. Comm., vol. 76, No. 1, pp. 174–182, (1977).
Tomoda, A., et al. Biochem. J., vol. 179, pp. 227–231, (1979).
Greenburg, A. G., Diagnostic Med., pp. 19–25, (1981).

*Primary Examiner*—Teddy S. Gron

[57] ABSTRACT

Blood gas control containing hemoglobin, a pH buffering agent, and a reduced pyridine nucleotide capable of participating in a reaction which reduces methemoglobin to normal hemoglobin.

15 Claims, 1 Drawing Figure

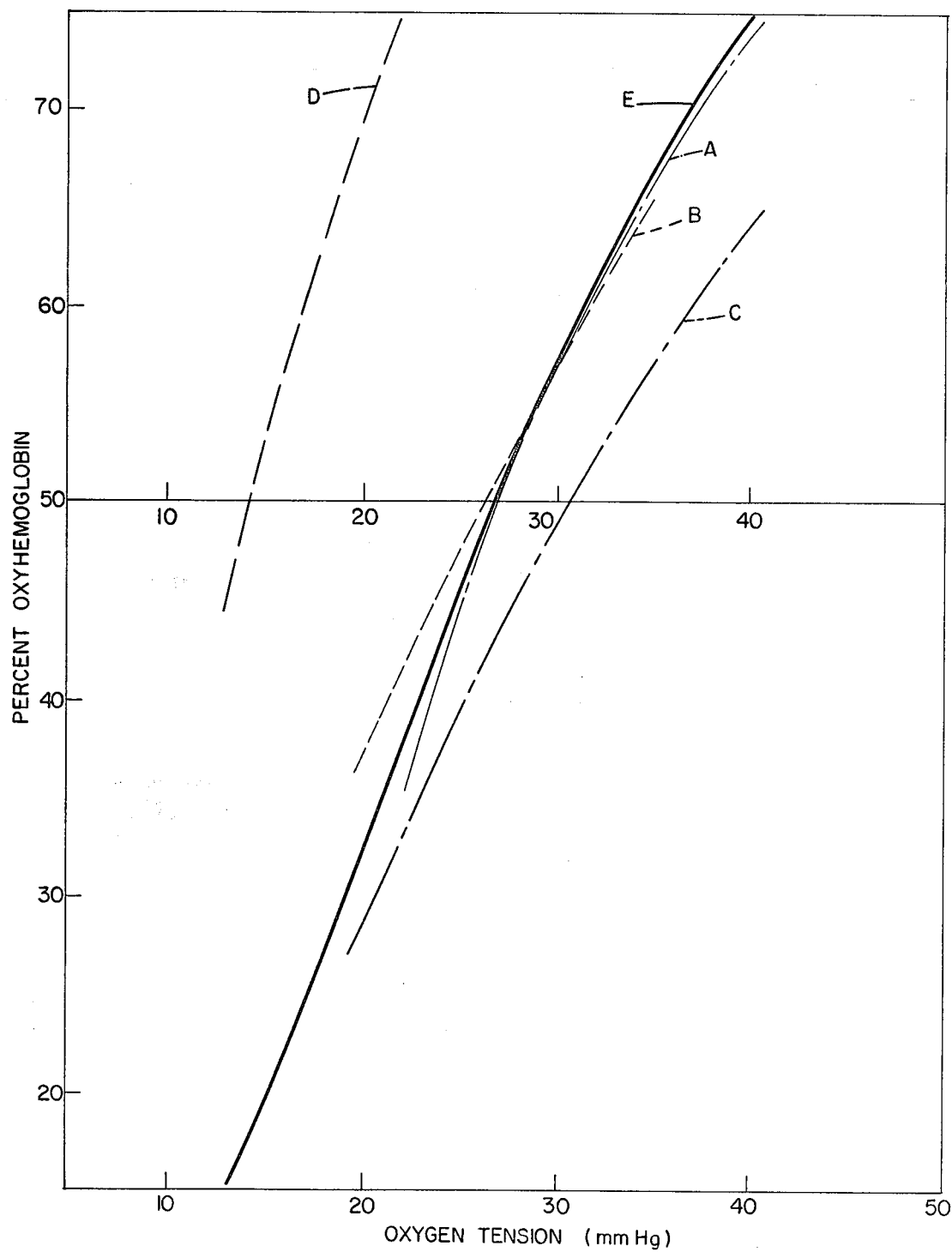

HEMOGLOBIN-BASED BLOOD GAS CONTROL

This invention relates to control liquids for quality control and/or calibration of equipment for the analysis of blood gas and the like.

Blood gas analyzers are utilized to measure parameters of blood such as pH, partial pressure of carbon dioxide (expressed as $pCO_2$), and partial pressure of oxygen (expressed as $pO_2$). Such blood gas analyzers require frequent calibration and quality control checks to ensure that the analyzer is operating properly and accurately. In connection with such quality control and calibration procedures, it is convenient to use a prepared control liquid of constant, known composition to monitor the accuracy of such analyzers.

Such control liquids should contain a component which can reversibly bind oxygen. Generally, this component can be either an artificial or a blood-derived material.

The usefulness of hemoglobin-based blood gas control liquids is limited by the autoxidation of the hemoglobin molecule to methemoglobin, which cannot reversibly bind oxygen. When the methemoglobin content increases, the oxyhemoglobin dissociation curve shifts to the left with an apparent fading of the sigmoid-shaped inflection to a hyperbolic curve; thus, the liquid's utility as a blood gas control is compromised. Stable methemoglobin values in such liquids are also important when the liquid is used to calibrate the various hemoglobin channels of an analyzer such as the Instrumentation Laboratory "CO-OXIMETER" analyzer.

We have discovered that the methemoglobin level in a hemoglobin-based control liquid can be controlled by the addition to the liquid of a reduced pyridine nucleotide or by the addition of a system for generating a reduced pyridine nucleotide, and that this addition does not adversely affect the other blood gas control functions of the liquid. NADH and NADPH are the preferred reduced nucleotides, and NADH, being more effective than NADPH, is most preferred. The addition of a generating system, including one or more substrates and one or more enzymes reactive with the substrates, is preferred over the simple addition of NADH or NADPH because a generating system provides a longer-lasting capacity to control the methemoglobin level, NADH or NADPH molecules being replenished by the system as other molecules are oxidized.

Other suitable pyridine nucleotides which can be used to generate suitable reduced nucleotides are the following NAD analogs: 3-acetylpyridine-adenine dinucleotide (3-AP-NAD); 3-pyridinealdehyde-adenine dinucleotide (3-PA-NAD); thionicotinamide-adenine dinucleotide (Thio-NAD); nicotinamide-hypoxanthine dinucleotide (Deamino-NAD); 3-acetylpyridine-hypoxanthine dinucleotide (3-AP-Deam-NAD); and 3-pyridinealdehyde-hypoxanthine dinucleotide (3-PA-Deam-NAD).

These are available commercially but are less preferred than an NADH generating system because of their comparatively greater expense.

The hemoglobin-based control liquid of the invention can be further improved by the addition of an organic phosphate capable of increasing and stabilizing the oxygen buffering capacity ($P_{50}$) of the liquid, preferably to the level found in normal blood, about 27 mm Hg. The preferred organic phosphate is inositol hexaphosphate (IHP), which provides the further advantage of enhancing the reduction of methemoglobin to normal hemoglobin.

Other suitable organic phosphates are adenosine triphosphate, adenosine disphosphate, adenosine monophosphate, guanidine triphosphate, guanidine monophosphate, 2, 3-diphosphoglycerate, ribose-5-phosphate, and pyridoxine-5-phosphate. Suitable inorganic phosphates are pyrophosphate, tripolyphosphate, tetrametaphosphate, and hexametaphosphate.

In control liquids of the invention which employ NADH or NADPH it is preferred that the liquid contain an active methemoglobin reductase, an enzyme which can employ NADH and NADPH as electron donors and which is involved in a mechanism by which NADH and NADPH reduce methemoglobin to normal hemoglobin in mammalian blood. Methemoglobin reductases are naturally present in red blood cell hemolysate, and additional enzyme can be obtained from a biochemical supply company such as CalBiochem-Behring, LaJolla, CA, and can be added to the blood gas control liquid as needed for maintenance of the desired methemoglobin level. The action of methemoglobin reductase is enhanced by the presence of the aforementioned organic and inorganic phosphates.

The blood gas control liquid of the invention contains, in addition to hemoglobin and the reduced pyridine nucleotide or generating system therefor, at least one pH buffering agent. The liquid can also contain a base for raising the pH of the liquid to between about 7.0 and 8.0, and a preservative in a concentration sufficient to inhibit microbiol growth without impairing quality control functions. The preferred preservative is 2-phenoxyethanol. The liquid is preferably supplied enclosed in gas-tight, sealed ampuls, and contains known concentrations of carbon dioxide and oxygen.

A number of enzyme systems are known which are capable of generating NADH or NADPH and which are suitable for use in the blood gas control liquid of the invention. Suitable systems are listed under the heading "Oxidoreductases" in the Enzyme Commission Table of Enzymes. In the systems listed therein, NAD and NADP act as proton acceptors and thus are converted to the desired reduced compounds NADH or NADPH.

The NADH-generating system we currently prefer is illustrated below:

L-lactic acid +

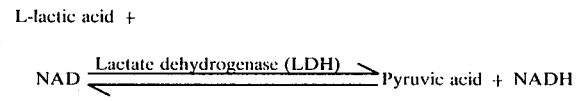

NAD ⇌ Pyruvic acid + NADH (via Lactate dehydrogenase (LDH))

Although the theoretically favored direction of the above reaction is right to left, the use of NADH as an electron donor for methemoglobin reductase, which reduces methemoglobin, may shift the equilibrium toward the right in the hemoglobin-based blood gas control. The reaction rate can be controlled by adjusting the relative concentrations of the reactants on the left side of the equation, to continuously provide the desired amount of NADH. Levels of NAD higher than about 1.0 mg NAD per ml liquid, however, are not desirable because such levels can cause an undesirable decrease in pH over time; about 0.5 to 1.0 mg NAD per ml liquid is therefore preferred.

Hemolysate, the preferred source of hemoglobin, contains L-lactic acid, LDH, and methemoglobin reductase, making it in some cases unnecessary to add much, if any, of these components when hemolysate is used. If commercially available powdered hemoglobin is used, however, these components must be provided from commercial sources.

A preservative should be present in a concentration of at least 0.2%, and most preferably at least 0.4%, by volume, to ensure that no microbiol growth occurs. The most preferred preservative is 2-phenoxyethanol. Other suitable preservatives are those containing 6-acetoxy-2, 4-dimethyl-m-dioxane; o-phenylphenol, 2-[(hydroxymethyl)amino]-2methylpropanol; alkyl-p-hydroxybenzoate; o-phenylphenate (sodium-o-phenylphenate tetrahydrate); 2-[(hydroxymethyl)amino]ethanol; 3,5-dimethyl-trihydro-1,3,5-2H-thiadiazine-2-thione; 1,2-dibromo-2,4-dicyanobutane; or benzyl bromoacetate. Antibiotics, such as gentamycin sulfate or polymyxin B can be used, but at greater expense. Alternatively, microbiol growth can be inhibited by employing fine-filter membrane sterilization.

The blood gas control liquids are preferably formulated to similate three physiological levels of pH, $pCO_2$, and $pO_2$ values. The choice of buffer used in the control liquids of the invention depends in part on whether the liquid is to be used for normal, acidosis, or alkalosis control. The buffer for the normal control should have a pKa appropriate for the optimal pH, 7.4, of that liquid. TAPSO (one of the Good buffers, named after their discoverer) is preferred for the normal control because its pKa=7.39 (at 37° C.). The chemical name of TAPSO is 3-[N-(tris-hydroxymethyl)methyl amino]-2-hydroxypropane sulfonic acid. Buffers having different pKa values may be more appropriate for acidosis and alkalosis controls; e.g. TES (N-tris(hydroxymethyl)-methyl-2-aminoethane sulfonic acid; pKa=7.50) and BES (N, N-bis-(2-Hydroxyethyl)-2-aminoethane sulfonic acid; pKa=7.15) may be used, respectively, in those liquids. Other buffers having pKa values between 7 and 8 are DIPSO (3-[N-bis-(hydroxyethyl)-amino]-2-hydroxypropane sulfonic acid; pKa=7.35); HEPES (N-2-hydroxyethylpiperazine-N'-2-ethane sulfonic acid; pKa=7.55); HEPPSO (N-hydroxyethylpiperazine-N-2-hydroxypropane sulfonic acid; pKa =7.73); MOPS (3-(N-Morpholino)-propane sulfonic acid; pKa=7.20); and POPSO (Piperazine-N,N'-bis-(2-hydroxypropane sulfonic acid; pKa=7.63). Final buffer concentrations will normally range between 0.05 M and 0.15 M.

Other features and advantages of the invention will be seen as the following description of a particular embodiment progresses, in connection with the drawing, in which:

The FIGURE is a graph of the relation between oxygen tension and percent oxyhemoglobin in five hemoglobin-containing liquid samples.

DESCRIPTION OF PARTICULAR EMBODIMENT

A normal blood gas control liquid is made as follows. First, hemolysate is prepared by centrifuging human heparinized whole blood, at 4° C., at 270 g for 15 minutes to remove the plasma. Blood in ACD or CPDA solutions can also be used. The red blood cells are then washed twice with cold 0.9% NaCl and then lysed with 0.1 M–0.15 M TAPSO, pH 8. The volumetric proportion of buffer to red blood cells is between 1:3 and 1:1, depending on the level of hemoglobin desired in the final product. Generally, the hemoglobin concentration is lowest for the acidosis control, higher for the normal control, and highest for the alkalosis control. Total hemoglobin concentration ranges typically are: acidosis: 8–10 g/dL; normal: 14–16 g/dL; alkalosis: 18–20 g/dL. The hemoglobin level in a sample can be lowered to a desired level by diluting the sample with buffer. The hemolysate is then extracted with one-quarter volume of toluene and allowed to sit overnight at 4° C. The separated hemolysate is then centrifuged at 1,500 g for 30 minutes to remove any remaining cellular debris, and then at 30,000 g for 90 minutes to remove traces of stroma. The pH is adjusted as desired with dilute NaOH.

The desired additives are then mixed into the hemoglobin samples. Because L-lactic acid, LDH, and methemoglobin reductase are normally present endogenously in hemolysate, in many cases only NAD and IHP need be added in order to maintain low methemoglobin levels for several months. Additional LDH and methemoglobin reductase are added, if necessary, to give concentrations of between five and fifteen, most preferably 7, units per ml of liquid. L-lactic can also be added, if necessary, to give a concentration between 0.02 M and 0.06 M. Lactic acid is added in a neutralized, concentrated buffer solution along with NAD and IHP. LDH is available from Boehringer Mannheim Biochemicals, Indianapolis, IN, and lactic acid is available from Sigma Chemical Co., St. Louis, MO. NAD is added to give a concentration between 0.14 mM and 1.4 mM, most preferably 0.7 mM, (0.1 to 1 mg/ml liquid) and IHP is added to give a concentration of between 1.0 mM and 1.6 mM, most preferably 1.4 mM. Final adjustment of pH is then carried out by the addition of dilute (1 N) NaOH. This sometimes results in the formation of a precipitate, which is removed by centrifugation at 1,500 g for 30 minutes, or by filtration. If desired, membrane sterilization is then carried out using sterile 0.22 M filters attached to syringes.

The $P_{50}$, i.e., the oxygen tension at which hemoglobin was 50% oxygenated, was measured in samples which were withdrawn after tonometry in an Instrumentation Laboratory Model 237 Tonometer with a gas mixture of 5.1% $CO_2$/2.8% $O_2$, and which were found to have oxyhemoglobin values of 40% to 60%. The results are shown in the FIGURE, in which curve A represents the sample just described; curve B represents a sample prepared as just described and having in addition a small amount of the preservative 2-phenoxyethanol; curve C represents a sample as just described except that a greater amount of IHP is added; curve D represents hemolysate containing no additives; and curve E represents whole blood, having an ideal $P_{50}$=27. As is shown in the FIGURE, curves A and B come very close to the ideal $P_{50}$ of 27. Tests performed to determine the stability of the $P_{50}$ indicated that, for samples represented by curve A in the FIGURE, the $P_{50}$ after 7 months was approximately 28, while that for the curve C samples was about 30.5.

Improved pH control is provided in the liquids of the invention by the addition of $NaHCO_3$ during tonometry. The concentration of $NaHCO_3$, as well as the percentage of $O_2$ and $CO_2$, varies, depending on whether the liquid is normal, alkalosis, or acidosis. Below are approximate preferred values.

|  | pH | % $O_2$ | % $CO_2$ | $NaHCO_3$ |
|---|---|---|---|---|
| Acidosis | 7.15–7.25 | 3.3 | 5.0 | 30.6 mM |
| Normal | 7.38–7.42 | 5.1 | 2.8 | 21 mM |

-continued

|  | pH | % O$_2$ | % CO$_2$ | NaHCO$_3$ |
|---|---|---|---|---|
| Alkalosis | 7.50–7.60 | 10.0 | 1.4 | 18.6 mM |

While a particular embodiment of the invention has been shown and described, various modifications will be apparent to those skilled in the art. Therefore it is not intended that the invention be limited to the disclosed embodiment or to details thereof and departures may be made therefrom within the spirit and scope of the invention.

What is claimed is:

1. A control liquid having known pH, pCO$_2$, and pO$_2$ for a blood gas analyzer or the like comprising
   hemoglobin,
   a pH buffering agent, and
   a reduced pyridine nucleotide capable of participating in a reaction which reduces methemoglobin to normal hemoglobin.

2. The control liquid of claim 1 and further including methemoglobin reductase and wherein said reduced pyridine nucleotide is NADPH or NADH.

3. The control liquid of claim 2 wherein said NADH or NADPH is provided by an NADH or NADPH generating system comprising one or more substrates and one or more enzymes reactive with said one or more substrates to generate sufficient NADH or NADPH to control the level of said methemoglobin in said control liquid.

4. The control liquid of claim 3 wherein said NADH or NADPH generating system is an NADH generating system comprising the chemical components L-lactic acid, NAD, and lactate dehydrogenase (LDH), said chemical components being present in amounts and proportions sufficient to generate said NADH according to the following reaction:

L-lactic acid + NAD $\xrightarrow{\text{LDH}}$ pyruvic acid + NADH.

5. The control liquid of claim 1, further comprising a methemoglobin reductase and an organic phosphate capable of increasing and stabilizing the P$_{50}$ of said liquid.

6. The control liquid of claim 5 wherein said organic phosphate is inositol hexaphosphate.

7. The control liquid of claim 1, further comprising a base for raising the pH of said liquid to between about 7.0 and 8.0.

8. The control liquid of claim 1, said liquid being provided in a sealed container, said control liquid having a pH in the range of 7.0 to 8.0, carbon dioxide in the range of 1–7%, and oxygen in the range of 2–12%.

9. The control liquid of claim 1 further comprising a preservative present in a concentration sufficient to inhibit microbial growth in said liquid without impairing the quality control functions of said liquid.

10. The control liquid of claim 9 wherein said preservative is 2-phenoxyethanol.

11. The control liquid of claim 4, wherein
    said hemoglobin is provided as a component of a mammalian erythrocyte hemolysate which also contains said methemoglobin reductase, said hemolysate and said pH buffering agent being present in the respective proportions of between 1:1 and 3:1, by volume,
    said NAD is present in the concentration of between 0.1 mg and 1.0 mg per ml of liquid,
    said methemoglobin reductase is present in the concentration of between five and fifteen units per ml of liquid,
    said LDH is present in the concentration of between five and fifteen units per ml of liquid,
    said L-lactic acid is present in the concentration of between 0.02 M and 0.06 M per, and
    said pH buffering agent is TAPSO, BES, or TES in a concentration of between 0.05 M and 0.15 M.

12. The control liquid of claim 11, further comprising an organic phosphate capable of increasing and stabilizing the P$_{50}$ of said liquid, and a preservative present in a concentration sufficient to inhibit microbial growth in said liquid without impairing the quality control functions of said liquid.

13. The control liquid of claim 12 wherein said organic phosphate is inositol hexaphosphate and said preservative is 2-phenoxyethanol.

14. The control liquid of claim 13 wherein
    said hemolysate and said pH buffering agent are present in the respective proportions of 1:1, by volume,
    said LDH is present in the concentration of 7 units per ml of liquid,
    said L-lactic acid is present in the concentration of 0.04 M,
    said methemoglobin reductase is present in the concentration of 7 units per ml of liquid,
    said inositol hexaphosphate is present in the concentration of 1.4 mM,
    said NAD is present in the concentration of 0.5 mg per ml of liquid, and
    said 2-phenoxyethanol is present in the concentration of 0.4%, by volume.

15. The control liquid of any one of claims 1, 4 or 14 wherein said liquid is in a sealed container and has a hemoglobin content in the range of 6–22 g/dL, a pH in the range of 7.0 to 8.0, a carbon dioxide content in the range of 1–7%, and an oxygen content in the range of 2–12%.

* * * * *